(12) United States Patent
Yasunaga et al.

(10) Patent No.: US 8,038,108 B2
(45) Date of Patent: Oct. 18, 2011

(54) SUPPORTING APPARATUS FOR MEDICAL INSTRUMENT

(75) Inventors: Koji Yasunaga, Hino (JP); Kenji Harano, Hachioji (JP); Noriaki Kanazawa, Kokubunji (JP)

(73) Assignee: Olympus Medical Systems Corp. (JP)

( * ) Notice: Subject to any disclaimer, the term of this patent is extended or adjusted under 35 U.S.C. 154(b) by 186 days.

(21) Appl. No.: 12/419,510

(22) Filed: Apr. 7, 2009

(65) Prior Publication Data

US 2009/0283647 A1 Nov. 19, 2009

(30) Foreign Application Priority Data

May 15, 2008 (JP) ................................ 2008-128680

(51) Int. Cl.
*A61B 19/00* (2006.01)
(52) U.S. Cl. ............... 248/123.2; 248/585; 248/281.11; 248/280.11; 359/384; 606/130; 606/167
(58) Field of Classification Search .............. 248/123.2, 248/280.11, 281.11, 585; 359/384; 606/130, 606/129, 167–170

See application file for complete search history.

(56) References Cited

U.S. PATENT DOCUMENTS

| | | | | |
|---|---|---|---|---|
| 4,339,100 A * | 7/1982 | Heller et al. | ............... | 248/123.2 |
| 4,344,595 A * | 8/1982 | Heller et al. | ............... | 248/542 |
| 5,173,802 A * | 12/1992 | Heller | ............... | 359/384 |
| 5,186,422 A | 2/1993 | Nakamura | | |
| 5,205,522 A * | 4/1993 | Nakamura | ............... | 248/123.11 |
| 5,373,583 A * | 12/1994 | Birum | ............... | 2/10 |
| 5,441,505 A * | 8/1995 | Nakamura | ............... | 606/130 |
| 5,480,114 A * | 1/1996 | Nakamura | ............... | 248/123.2 |
| 5,528,417 A * | 6/1996 | Nakamura | ............... | 359/384 |
| 5,651,718 A * | 7/1997 | Nakamura | ............... | 248/123.2 |
| 5,667,186 A | 9/1997 | Luber et al. | | |
| 5,713,545 A * | 2/1998 | Nakamura | ............... | 248/123.2 |
| 5,812,301 A * | 9/1998 | Nakamura | ............... | 359/384 |
| 5,818,638 A * | 10/1998 | Nakamura | ............... | 359/384 |

(Continued)

FOREIGN PATENT DOCUMENTS

EP 0 656 194 6/1995

(Continued)

OTHER PUBLICATIONS

Search Report issued by the European Patent Office in connection with corresponding application No. EP 09 005 242.3 on Aug. 25, 2009. Letter from German associate dated Sep. 1, 2009 forwarding the European Search Report dated Aug. 25, 2009 to Japanese associate, including discussion of relevancy thereof.

*Primary Examiner* — Terrell McKinnon
*Assistant Examiner* — Daniel J Breslin
(74) *Attorney, Agent, or Firm* — Ostrolenk Faber LLP

(57) ABSTRACT

An apparatus for supporting a medical instrument includes an arm, which has a support portion to support a medical instrument at one end, and an intermediate portion of which is supported by a base portion via a support column. The arm moves the support portion horizontally and vertically. The apparatus also includes a rotary connecting member, which is provided at a second end of the arm and moves to a position corresponding to a position to which the support portion has been moved. The apparatus further includes a counterweight, which is connected to the support column to be immovable in the horizontal directions and movable in the vertical directions, and generates vertically downward force. The rotary connecting member is connected to the counterweight so as to be movable in the horizontal directions relative to the counterweight and movable in the vertical directions together with the counterweight.

10 Claims, 5 Drawing Sheets

U.S. PATENT DOCUMENTS

| | | | | |
|---|---|---|---|---|
| 5,825,536 | A * | 10/1998 | Yasunaga et al. | 359/384 |
| 6,045,104 | A * | 4/2000 | Nakamura et al. | 248/280.11 |
| 6,050,530 | A * | 4/2000 | Nakamura | 248/123.2 |
| 6,105,909 | A * | 8/2000 | Wirth et al. | 248/123.2 |
| 6,646,798 | B2 * | 11/2003 | Schmidt et al. | 359/382 |
| 6,833,950 | B2 * | 12/2004 | Schmidt | 359/384 |
| 7,018,386 | B2 * | 3/2006 | Nakamura | 606/130 |
| 7,283,296 | B2 * | 10/2007 | Nozawa et al. | 359/384 |
| 7,461,824 | B2 * | 12/2008 | Poxleitner et al. | 248/278.1 |
| 7,472,872 | B2 * | 1/2009 | Nakamura | 248/123.2 |
| 7,724,428 | B2 * | 5/2010 | Nakamura et al. | 359/384 |
| 2002/0121577 | A1 * | 9/2002 | Metelski | 248/123.11 |
| 2004/0138524 | A1 * | 7/2004 | Ueda et al. | 600/102 |
| 2004/0190131 | A1 * | 9/2004 | Brenner et al. | 359/384 |
| 2005/0167550 | A1 | 8/2005 | Poxleitner et al. | |
| 2006/0291044 | A1 * | 12/2006 | Nozawa et al. | 359/382 |

FOREIGN PATENT DOCUMENTS

| | | |
|---|---|---|
| EP | 1 915 965 | 4/2008 |
| JP | 63-36481 | 7/1988 |
| JP | 7-143995 | 6/1995 |
| JP | 7-227398 | 8/1995 |
| JP | 2001-258903 | 9/2001 |

\* cited by examiner

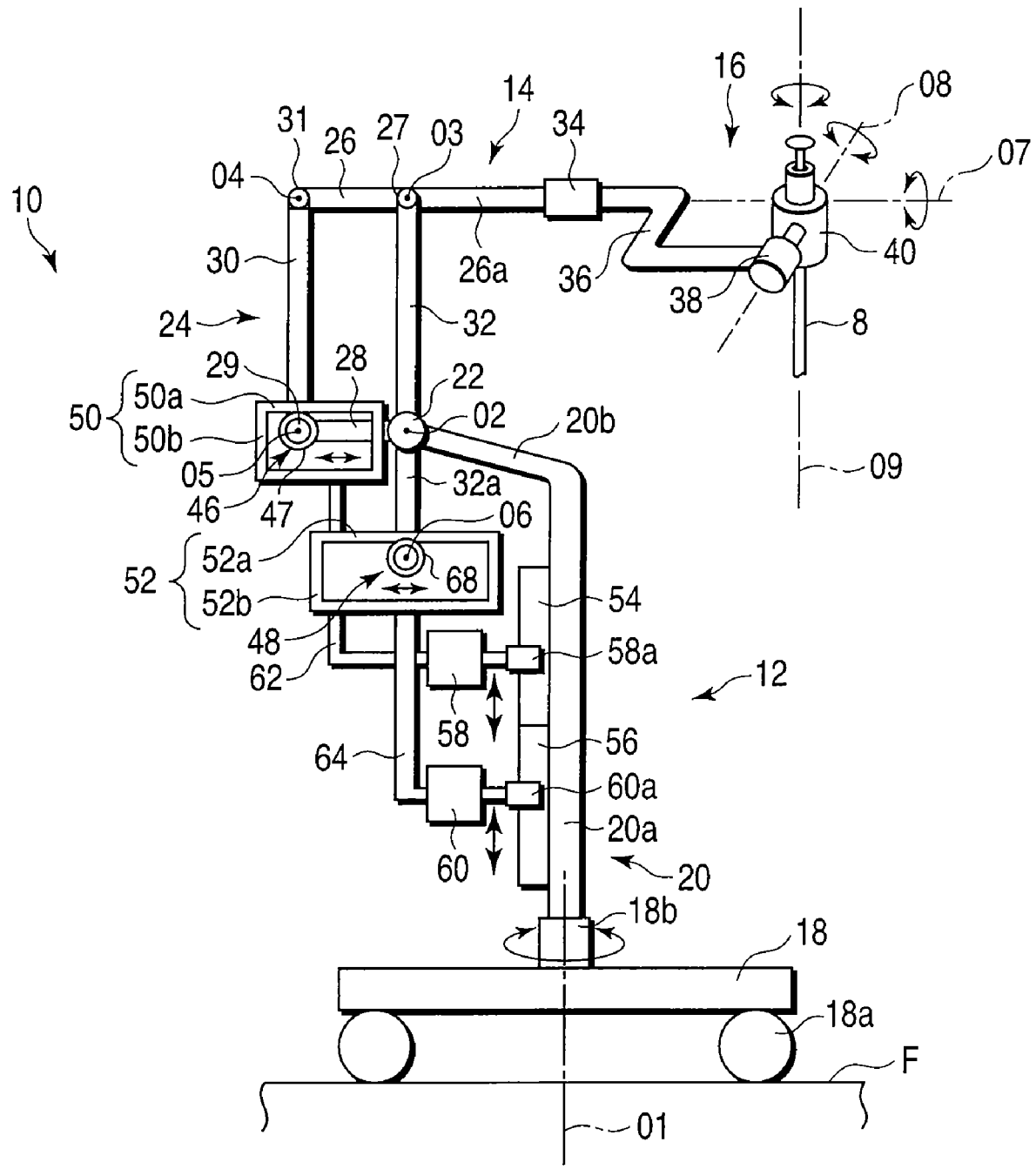
F I G. 1

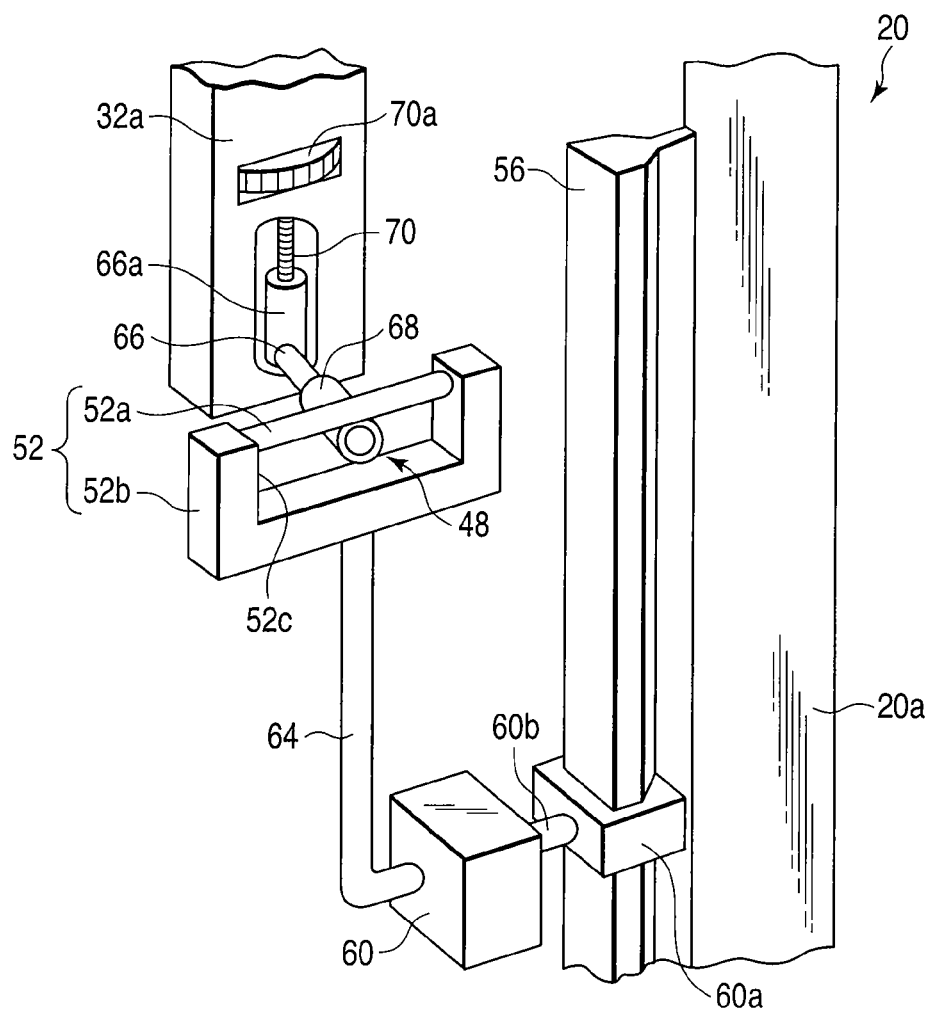
F I G. 2
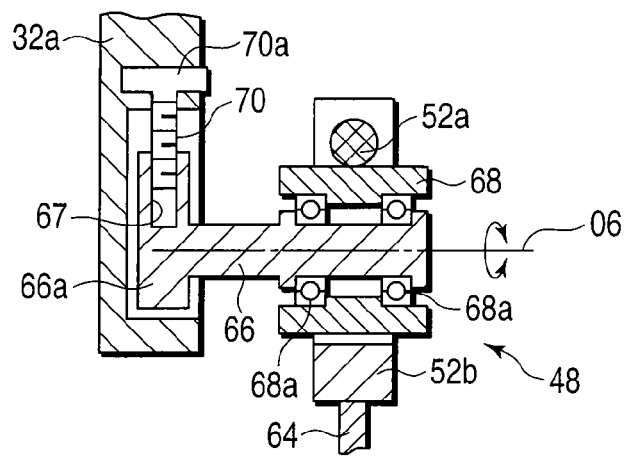
F I G. 3

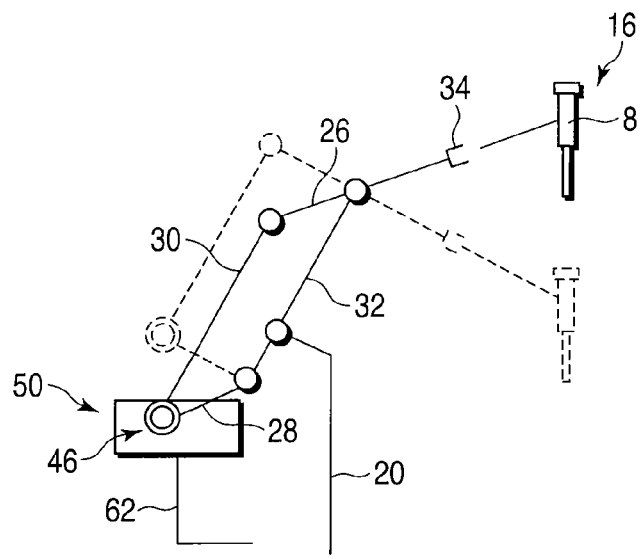
F I G. 6
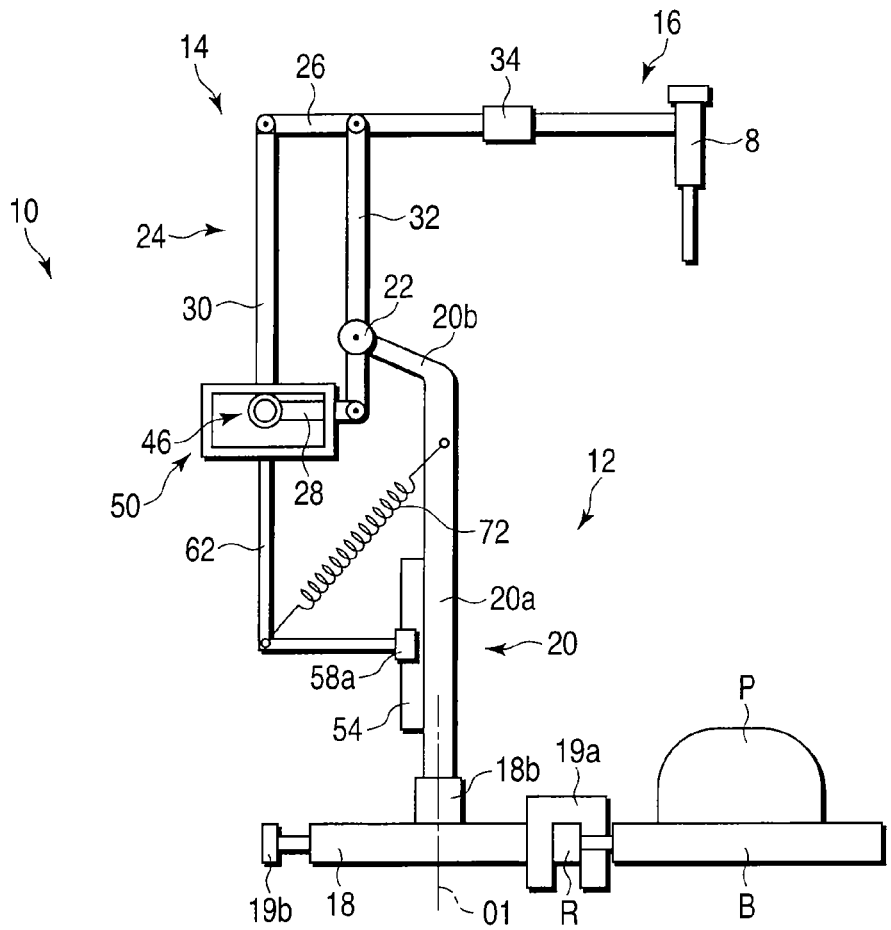
F I G. 7

SUPPORTING APPARATUS FOR MEDICAL INSTRUMENT

CROSS-REFERENCE TO RELATED APPLICATIONS

This application is based upon and claims the benefit of priority from prior Japanese Patent Application No. 2008-128680, filed May 15, 2008, the entire contents of which are incorporated herein by reference.

BACKGROUND OF THE INVENTION

1. Field of the Invention

The present invention relates to a supporting apparatus for a medical instrument, which is capable of maintaining the supported medical instrument at a desired position.

2. Description of the Related Art

For example, Jpn. Pat. Appln. KOKOKU Publication No. 63-36481 and Jpn. Pat. Appln. KOKAI Publication No. 7-143995 disclose a supporting apparatus for a medical instrument. The medical instrument supporting apparatus disclosed in these publications supports a medical instrument, such as an endoscope or a surgical microscope, on an end of an arm of the apparatus, smoothly moves it to a desired position and maintains it at the position. The conventional medical instrument supporting apparatus is of a counterbalance system, in which a counterweight is located on the other end of the arm beyond a fulcrum to keep the balance with the medical instrument.

In this system, for example, one of four link members forming a parallelogram link is rotatably attached to a support column. A support arm which holds a surgical microscope is located at one end of the link member attached to the support column, and a counterweight is located on the other end of the link member beyond the support column. The counterweight is moved horizontally and vertically in association with horizontal and vertical movements of the support arm. Thus, the balance between the surgical microscope and the counterweight is kept to carry out delicate surgical operations.

Jpn. Pat. Appln. KOKAI Publication No. 7-227398 and Jpn. Pat. Appln. KOKAI Publication No. 2001-258903 discloses a supporting apparatus, which adjusts the balance between an endoscope and a counterweight via a similar parallelogram link to smoothly and exactly move the endoscope to observe a subject part in the abdominal cavity and fix it at a required position.

In the conventional supporting apparatuses for medical instruments as described above, the counterweight is moved in association with the movement of the medical instrument, such as an endoscope or a surgical microscope. For example, if the medical instrument is projected horizontally in one direction, the counterweight must be projected in the opposite direction. In an operation room, a number of various apparatuses are placed and a number of assistants or nurses are required to do their works in a limited space where a patient lies. Therefore, if the counterweight projects in the direction opposite from the medical instrument, it may be brought into contact with another apparatus or obstruct works of the nurses or the like. Further, if the movement of the counterweight is limited, it will be difficult to obtain a satisfactory field of view of the operator.

BRIEF SUMMARY OF THE INVENTION

According to an aspect of the present invention, there is provided an apparatus for supporting a medical instrument, comprising: a support column placed in one of a floor, a ceiling, a medical trolley and a bed; an arm supported by the support column and having a first end to which a support portion to support a medical instrument and a second end, the arm being configured to move the support portion in horizontal directions and vertical directions relative to the support column; a position changing member that is provided on a side of the second end of the arm, moves in accordance with movement of the support portion to a position corresponding to a position to which the support portion has been moved; and a counterweight system, which is configured to be immovable in the horizontal directions and movable in the vertical directions relative to the support column, and generates vertically downward force, wherein the position changing member is connected to the counterweight system so as to be movable in the horizontal directions relative to the counterweight system and movable in the vertical directions together with the counterweight system, and when the first end of the arm moves, the position changing member keeps a balanced state between the medical instrument supported by the support portion and the counterweight system.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing the overall structure of a medical instrument supporting apparatus according to an embodiment of the present invention.

FIG. 2 is an explanatory diagram for explaining an operation of a position changing member and a weight connecting portion of the medical instrument supporting apparatus shown in FIG. 1.

FIG. 3 is an explanatory diagram showing a cross section of the position changing member and the weight connecting portion shown in FIG. 2.

FIG. 6 is an explanatory diagram for explaining a function of the arm of the medical instrument supporting apparatus shown in FIG. 4, moving the support portion vertically.

FIG. 7 is a schematic diagram showing a medical instrument supporting apparatus, which can be attached to a bed, according to still another embodiment.

DETAILED DESCRIPTION OF THE INVENTION

Figure 4:
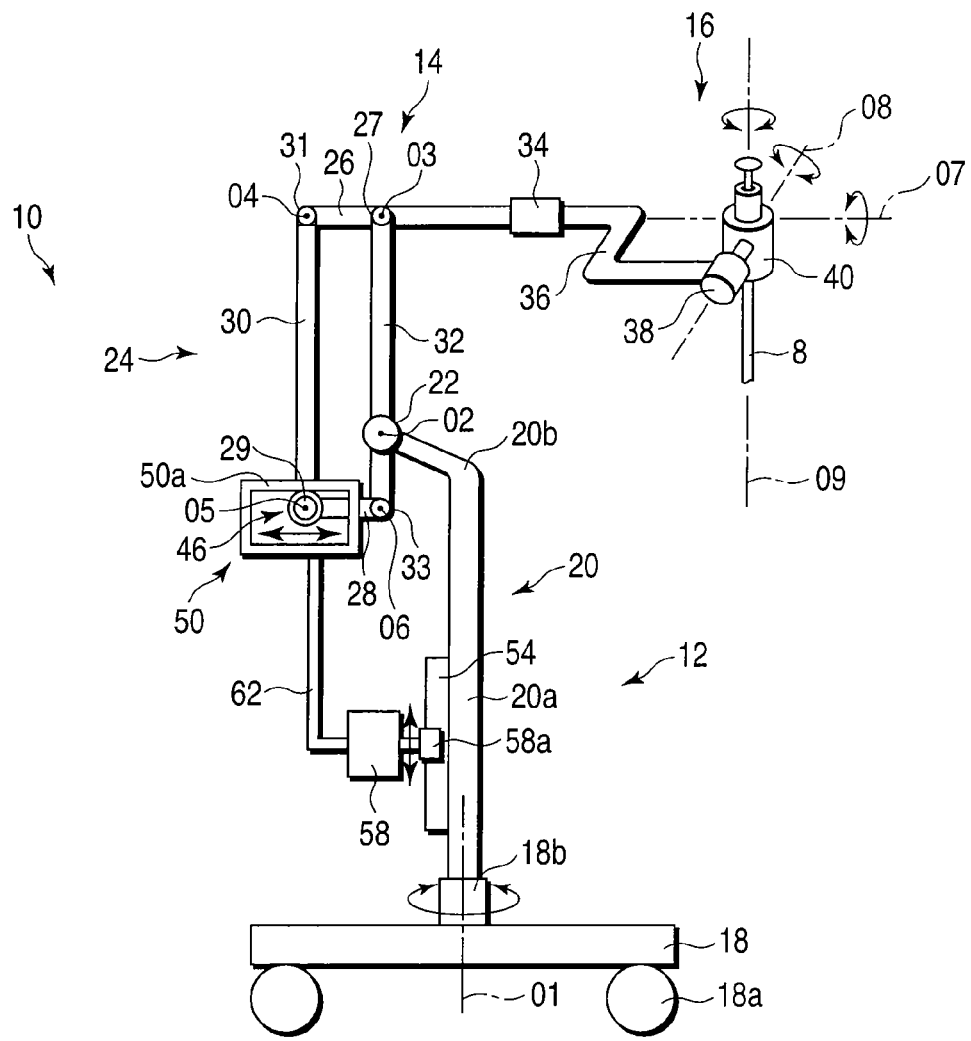
FIG. 4 is a schematic diagram showing a lighter medical instrument supporting apparatus according to another embodiment.

FIGS. 1 to 3 show a medical instrument supporting apparatus 10 according to an embodiment of the present invention.

The medical instrument supporting apparatus 10 of this embodiment is placed in an operation room, inspection room or treatment room. It supports a medical instrument 8 such as a microscope, endoscope, medical treatment tool or medical display. The apparatus 10 is configured to freely change the position of the medical instrument 8 in three-dimensional space regardless of the ambient environment to make full use of the functions of the medical instrument 8 and reduce the fatigue of an operator (for example, a doctor) to a minimum.

As shown in FIG. 1, the medical instrument supporting apparatus 10 of this embodiment has a base portion 12, which is placed on a floor F of a medical room and rotatably supports a middle portion of an arm 14. With this configuration, the apparatus 10 is capable of moving the medical instrument 8, for example, an endoscope attached to a support portion 16 at an end of the arm 14, freely in horizontal and vertical directions.

The base portion 12 has a block-shaped or plate-like base 18, which is movable on the floor F with a plurality of casters 18a provided on the bottom surface of the base portion 12. The base portion 12 also has a support column 20 extending upward from the upper surface of the base 18 and rotatable relative to the base 18 about a vertical axis O1. The base portion 12 may include suitable braking means or fixing means to prevent the casters 18a from rotating or to prevent the base 18 from moving relative to the floor.

The support column 20 has an upright portion 20a extending from the base 18 along the vertical axis O1 and an inclined portion 20b inclined with respect to the vertical axis O1 above the upright portion 20a. A support member 22 is located at a distal end of the inclined portion 20b to support the arm 14 to be rotatable about a horizontal axis O2. When the support column 20 rotates relative to the base 18, a rotational force adjusting portion 18b can adjust the amount of rotational force, that is, torque necessary for the rotation. Thus, the support column 20 can be rotated about the vertical axis O1 to a required position and maintained at that position. When torque greater than the value set by the rotational force adjusting portion 18b is applied, the support column 20 can rotate about the vertical axis O1.

The arm 14 supported at the distal end of the inclined portion 20b of the support column 20 has a link mechanism portion 24 comprising a parallelogram link mechanism. The link mechanism portion 24 is located in a plane perpendicular to the horizontal axis O2. It has an upper rod 26 and a lower rod 28 parallel to each other, and a connecting rod 30 and a pivot rod 32 parallel to each other. The pivot rod 32 is rotatably supported by the support column 20 via the support member 22. A vertical extension portion 32a of the pivot rod 32 extends across the support member 22 toward the base 18.

In the link mechanism portion 24, a joint portion 27 rotatably connects the upper rod 26 and the pivot rod 32, a joint portion 31 rotatably connects the upper rod 26 and the connecting rod 30, and a joint portion 29 rotatably connects the lower rod 28 and the connecting rod 30. The support member 22 as a joint portion rotatably connects the lower rod 28 and the pivot rod 32. A horizontal axis O3 of the joint portion 27, a horizontal axis O4 of the joint portion 31 and a horizontal axis O5 of the joint portion 29 extend parallel to the horizontal axis O2 of the support member 22, all extending perpendicular to the plane of the drawing of FIG. 1.

The upper rod 26 of the link mechanism portion 24 has a horizontal extension portion 26a integrally extending from the rod 26 toward the vertical axis O1 across the joint portion 27 connecting the pivot rod 32. The support portion 16 is connected to the horizontal extension portion 26a via a rotational force adjusting portion 34 located at a distal end of the horizontal extending portion 26a. In this embodiment, the support portion 16 has a crank-shaped arm portion 36, a rotary force adjusting portion 38 located at a distal end of the arm portion 36 and a cylindrical distal end support member 40 connected to the rotary force adjusting portion 38. The medical instrument 8 such as an endoscope can be fixed inside an inner hole of the distal end support member 40. The distal end support member 40 is rotatable about a central axis O7 of the horizontal extension portion 26a formed integral with the upper rod 26 and the rotary force adjusting portion 34 and a central axis O8 of the rotary force adjusting portion 38. The amounts of force necessary to rotate the medical instrument 8 about the central axes O7 and O8 are adjusted by the rotary force adjusting portions 34 and 38.

It is preferable that the central axes O7 and O8 extend through a point on a central axis O9 of the inner hole of the distal end support member 40, and the three central axes O7, O8 and O9 are perpendicular to one another. It is also preferable that the distal end support member 40 be configured to move the medical instrument 8 through the inner hole along the axis O9, rotate it about the axis O9 and secure it in the posture at an axial position and a rotational position as required. Thus, the support portion 16 constitutes a tilting mechanism which rotates the medical instrument 8 about the central axes O7, O8 and O9 and tilts it in the directions of the three axes.

Because of the tilting mechanism capable of tilting the distal end support member 40 of the support portion 16 in the three axial directions, the posture as well as the position of the medical instrument 8 supported by the support portion 16 can be adjusted variously. In particular, in the case where the medical instrument 8 is at least one of a microscope, an endoscope, a medical display and a medical treatment tool, it is possible to make full use of the functions thereof, because the position and posture can be controlled accurately.

When the arm 14 having the structure as described above moves the support portion 16 in the vertical directions along the vertical axis O1 and rotates the link mechanism 24 about the horizontal axis O2 of the support member 22, the joint portion 29 of the link mechanism 24 moves in the vertical directions accordingly. When the support portion 16 is moved in the direction perpendicular to the vertical axis O1 (parallel to the central axis O7) and the link mechanism 24 is deformed, the distal end portion of the vertical extension portion 32a moves in the horizontal directions accordingly. When the support portion 16 moves in the horizontal and vertical directions, the joint portion 29 and the distal end portion of the vertical extension portion 32a move accordingly by the distance corresponding to the horizontal component and the vertical component.

The joint portion 29 and the distal end portion of the vertical extension portion 32a, which move according to the movement of the support portion 16, are respectively provided with rotary connecting members 46 and 48 as position changing members. The rotary connecting member 46 provided at the joint portion 29 has a cylindrical member 47 which freely rotates about the horizontal axis O5, and constitutes an interlocking member which moves interlocking with the rotation of the link mechanism 24 relative to the support column 20 about the horizontal axis O2. The rotary connecting member 48 provided at the distal end portion of the vertical extension portion 32a has a cylindrical member 68 (to be described later), which can freely rotate about a horizontal axis O6 parallel to the horizontal axis O2, and constitutes an interlocking member which moves interlocking with the deformation of the link mechanism 24. The rotary connecting members 46 and 48 function as position changing members, which engage with weight connecting portions 50 and 52 (to be described later) movable only in the vertical directions and which are moved by the link mechanism 24 to the positions corresponding to the position of the support portion 16 as the support portion 16 moves.

The amounts of movement of the rotary connecting members 46 and 48 from the stationary position, just before the position change, are proportional to the arm lengths, that is, the distances from the respective members to the horizontal axis O2 of the support member 22 which is the fulcrum. More specifically, the amount of movement of the joint portion 29, that is, the rotary connecting member 46, corresponding to the vertical movement of the distal end support member 40 is determined by the ratio of the distance between the axes O2 and O5 to the distance between the axes O3 and O8 on the axis O7. The amount of movement of the distal end portion of the vertical extension portion 32a, that is, the rotary connecting member 48, corresponding to the horizontal movement of the distal end support member 40 is determined by the ratio of the distance between the axes O2 and O6 to the distance between the axes O2 and O3.

The support column 20 supporting the arm 14 is provided with rail-shaped guides 54 and 56 extending along the vertical axis O1 on a side of the upright portion 20a and in parallel with each other. Counterweights 58 and 60 are respectively arranged on the guides 54 and 56 via connecting slides 58a and 60a, which are immovable in the horizontal directions and movable only in the vertical directions. The counterweights 58 and 60 are integrally connected to the weight connecting portions 50 and 52 via L-shaped shafts 62 and 64, and constitute a counterweight system together with the weight connecting portions 50 and 52. It is preferable that the counterweights 58 and 60 should not move horizontally outward and should be arranged on the same side as the inclined portion 20b of the support column 20 to keep the medical instrument supporting apparatus 10 compact.

As shown in FIG. 2, the guide 56 has a rail shape having a dovetail cross section. The connecting slide 60a has an engagement hole, which has a dovetail cross section and fits to the guide 56. Thus, the guide 56 is slidable only in the vertical directions without rattle and prevented from moving horizontally and rotating. The connecting slide 60a is integrally connected to the counterweight 60 via a short connecting shaft 60b. The counterweight 60 may be omitted, in which case the connecting slide 60a may serve as a counterweight.

As shown in FIGS. 2 and 3, the weight connecting portion 52 connected to the counterweight 60 via the L-shaped shaft 64 has a horizontal guide 52a having a circular cross section and engaging with the rotary connecting member 48. The weight connecting portion 52 also has a frame portion 52b having a pair of arm portions connected to the ends of the horizontal guide 52a and a central portion integrally connected to the upper end of the L-shaped shaft 64. The weight connecting portion 52 is supported by the L-shaped shaft 64, the counterweight 60, the connecting shaft 60b and the connecting slide 60a, such that the horizontal guide 52a is kept perpendicular to the horizontal axis O6 of the rotary connecting member 48 and the vertical axis O1. The rotary connecting member 48 is inserted in a substantially rectangular opening 52c defined by the horizontal guide 52a and the frame portion 52b, and thus fit to or engaged with the horizontal guide 52a, thereby connecting the link mechanism 24 and the counterweight 60.

In this embodiment, the weight connecting portions 50 and 52, the counterweight 58 and 60 and the L-shaped shafts 62 and 64 constitute a counterweight system, which generates vertically downward force.

The rotary connecting member 48 of this embodiment has the cylindrical member 68 attached to a peripheral portion of a distal end of a projecting shaft 66 so as to be rotatable about the horizontal axis O6 via two rotary bearings 68a. The projecting shaft 66 projects coaxially with the horizontal axis O6 from the distal end portion of the vertical extension portion 32a of the pivot rod 32. The cylindrical member 68 directly engages with the horizontal guide 52a in the opening 52c of the weight connecting portion 52, and can roll along the horizontal guide 52.

The projecting shaft 66 of the rotary connecting member 48 can make parallel displacement along the longitudinal direction of the vertical extension portion 32a, so that the distance between the horizontal axes O2 and O6 can be adjusted. For example, a screw hole 67 perpendicular to the horizontal axis O6 of the projecting shaft 66 may be formed a base portion 66a and a connecting position adjusting member, such as a screw shaft 70 attached to the vertical extension portion 32a, may be screwed in the screw hole 67. The projecting shaft 66 can be moved by operating the connecting position adjusting member. In this case, notches should preferably be formed in a head portion 70a of the shaft 70, so that the position of the rotary connecting member 48 can easily be adjusted from outside by operating the head portion 70a. The connecting position adjusting member may have any mechanism other than that shown in the drawings, if the function thereof is satisfactorily performed. In any case, the projecting shaft 66 keeps the horizontal axis O6 parallel with the horizontal axis O2 of the support member 22, which supports the vertical extension portion 32a to the support column 20.

Similarly, the rotary connecting member 46 provided at the joint portion 29 of the link mechanism 24 has the cylindrical member 47 rotatable about the horizontal axis O5 via rotary bearings (not shown). The cylindrical member 47 is located in an opening of the weight connecting portion 50 defined by a horizontal guide 50a and a frame portion 50b and engaged with the horizontal guide 50a. The counterweight 58 connected to the frame portion 50b of the weight connecting portion 50 via the L-shaped shaft 62, the connecting slide 58a and the guide 54 are formed in the same manner as the counterweight 60 connected to the weight connecting portion 52 via the L-shaped shaft 64, the connecting slide 60a and the guide 56.

The counterweights 58 and 60 may be formed integrally with the frame portions 50b and 52b of the weight connecting portions 50 and 52. The guides 54 and 56 may be of any shape that allows the connecting slides 58a and 60a, the counterweights 58 and 60 and the weight connecting portions 50 and 52 to move without interference with one another.

The medical instrument supporting apparatus 10 thus formed can hold the medical instrument 8 attached to the distal end support member 40 with the force set by the rotary force adjusting portions 34 and 38, freely rotate it about the axes O7 and O8, and keep it at a required position. The support portion 16 as a whole is balanced with the counterweights 58 and 60 via the arm 14. More specifically, the force exerted clockwise in FIG. 1 about the axis O2 on the support portion 16 is balanced with the force exerted counterclockwise on the counterweights 58 and 60 via the link mechanism 24 of the arm 14.

For example, in the balanced state shown in FIG. 1, the pivot rod 32 and the vertical extension portion 32a are arranged vertically in parallel with the vertical axis O1, and the rotary connecting member 48 is located in a neutral position under the horizontal axis O2 along the vertical line. The load of the counterweight 60 is exerted downward via the rotary connecting member 48 and the weight connecting portion 52 and does not generate force in either the clockwise or counterclockwise direction.

The lower rod 28 and the upper rod 26, to which the support portion 16 is fixed through the horizontal extension portion 26a, are arranged parallel with the floor F. The load of the counterweight 58 is exerted on the joint portion 29 connecting the lower rod 28 and the connecting rod 30 via the rotary connecting member 46, the weight connecting portion 50 and the L-shaped shaft 62. The product of the weight of the counterweight 58 and the horizontal distance (moment arm in mechanics) between the horizontal axes O2 and O5 generates rotation moment in the counterclockwise direction. This rotation moment in the counterclockwise direction is balanced with the rotation moment in the clockwise direction generated in the support portion 16.

When the support portion 16 is moved upward downward without rotating the pivot rod 32 and the vertical extension portion 32a, the link mechanism 24 rotates about the horizontal axis O2. The horizontal distance between the horizontal axes O2 and O5 is changed. The rotary connecting member 46, on which the load of the counterweight 58 is exerted, causes the cylindrical member 47 to roll along the horizontal guide 50a to a position corresponding to the horizontal distance between the horizontal axis O2 and the central axis O8 in the support portion 16 supporting the medical instrument 8. Since the ratio of the horizontal distance between the axis O8 and the axis O2 to the horizontal distance between the axis O5 and the axis O2 does not change, the balanced state between the support portion 16 and the counterweight 58 is maintained.

On the other hand, when the support portion 16 is moved in a horizontal direction parallel to the floor F from the balanced state shown in FIG. 1 and the link mechanism 24 is deformed, the upper rod 26 and the horizontal extension portion 26a, to which the support portion 16 is fixed, make parallel displacement relative to the lower rod 28. The pivot rod 32 and the vertical extension portion 32a pivot about the horizontal axis O2 of the support member 22 supporting the link mechanism 24. The lower rod 28 does not move, and accordingly, none of the rotary connecting member 46, the weight connecting portion 50, the L-shaped shaft 62, the counterweight 58 and the connecting slide 58a moves.

The rotary connecting member 48 provided at the distal end of the vertical extension portion 32a causes the cylindrical member 68 to roll on the horizontal guide 52a, while moving to draw an arc about the horizontal axis O2. Thus, the rotary connecting member 48 is displaced together with the weight connecting portion 52. In this time, the amount of movement of the rotary connecting member 48 and the amount of movement of the support portion 16 correspond to each other, and the directions of movements are opposite.

For example, when the support portion 16 makes rightward parallel displacement from the balanced state shown in FIG. 1, the rotation moment in the clockwise direction increases by the displacement. In this time, the rotary connecting member 48 moves leftward from the neutral position under the horizontal axis O2 along the vertical line. Then, rotation moment in the counterclockwise direction is generated by the product of the counterweight 60 and the horizontal distance between the horizontal axes O2 and O6 is added to rotation moment in the counterclockwise direction by the counterweight 58 exerted on the rotary connecting member 46. When the support portion 16 makes leftward parallel displacement, the rotary connecting member 48 moves rightward and generates rotation moment in the clockwise direction. The rotation moment in the clockwise direction by the counterweight 60 acts to reduce the rotation moment in the counterclockwise direction of the counterweight 58 and maintains the balance with the rotation moment of the support portion 16.

The balanced state as described above is maintained even when the support portion 16 is moved in horizontal and vertical directions simultaneously and the link mechanism 24 is both deformed and rotated. Further, even when the support column 20 is rotated about the vertical axis O1, the counterweights 58 and 60 can rotate along with the support column 20 while being arranged below the inclined portion 20b, so that the balanced state can be maintained. In any situation, the counterweights 58 and 60 do not project outside from the arm 14 in a horizontal direction.

To make the explanation simple, the balanced state in a case where the pivot rod 32 extends vertically as shown in FIG. 1 has been described. However, in whatever state the link mechanism 24 is rotated or deformed, the rotation connecting members 46 and 48 and the weight connecting portions 50 and 52 smoothly follow the movement of the support portion 16. It is clear that the counterweights 58 and 60 also move accordingly. In particular, since the rotary connecting members 46 and 48 have the cylindrical members 47 and 68 which are freely rotatable about the central axes O5 and O6 and the cylindrical members are configured to roll along the horizontal guides 50a and 52a, the counterweights smoothly follow the movement of the support portion 16.

Therefore, in the medical instrument supporting apparatus 10, when the support portion 16 supporting the medical instrument 8 moves horizontally and vertically relative to the support column 20 of the base portion 12, the rotary connecting members 46 and 48 as the position changing members located opposite from the support portion 16 are moved horizontally relative to the weight connecting portions 50 and 52 and the counterweights 58 and 60, which serve as a counterweight system and can move only vertically. Thus, the support portion 16 supporting the medical instrument 8 is kept in balance with the counterweights 58 and 60 via the arm 14. Therefore, the medical instrument 8 can freely be extended or contracted with excellent operability, regardless of the ambient environment, for example, even in a small space.

In particular, the counterweights 58 and 60 as the counterweight system move only in the vertical directions along the guides 54 and 56. Therefore, even when the support portion 16 is moved horizontally and vertical at the same time, constant load can be exerted on the support portion 16 via the arm 14 regardless of the location of the support portion 16. Thus, stable operation can be performed.

Since the arm 14 has the link mechanism 24 including the parallelogram link mechanism, the rotary connecting members 46 and 48 as the position changing members can accurately follow the movement of the support portion 16 supporting the medical instrument 8 and keep the balanced state.

Further, the position changing members are formed of the rotary connecting member 48 as a deformation associating member, which moves in association with the deformation of the link mechanism 24, and the rotary connecting member 46 as a rotation associating member, which moves in association with the rotation of the link mechanism 24 about the horizontal axis O2 relative to the support column 20. With this configuration, the movement of each of the rotary connecting members 46 and 48 is simplified. Therefore, it is possible to easily make various adjustments, for example, an adjustment of the balance by the screw shaft 70 and an adjustment of the weights or shapes of the counterweights 58 and 60.

Figure 5:
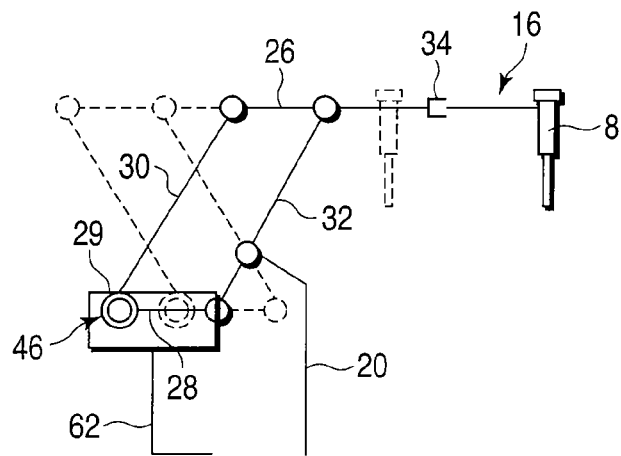
FIG. 5 is an explanatory diagram for explaining a function of an arm of the medical instrument supporting apparatus shown in FIG. 4, moving a support portion horizontally.

FIGS. 4 to 6 show a medical instrument supporting apparatus 10 according to another embodiment of the present invention. In the following descriptions, various embodiments or modifications are basically the same as the above embodiment shown in FIGS. 1 to 3. Therefore, the same parts are identified by the same reference numerals and detailed descriptions thereof are omitted.

In the embodiment shown in FIGS. 4 to 6, the counterweight system has only one counterweight 58, and does not have the counterweight 60.

In an arm 14, an intermediate portion of a pivot rod 32 of a link mechanism 24 is supported by a support column 20 via a support member 22. The arm 14 is rotatable about a horizontal axis O2. In the link mechanism 24, the pivot rod 32 and a lower rod 28 are connected by a joint portion 33, which is rotatable about a horizontal axis O6.

In the balanced state as shown in FIG. 4, for example, the pivot rod 32 and a connecting rod 30 are parallel with a vertical axis O1. When the support portion 16 is moved rightward as indicated by solid lines or leftward as indicated by broken lines as shown in FIG. 5, a rotary connecting member 46 provided at a joint portion 29 is moved to the left and right relative to a weight connecting portion 50. Thus, the rotary connecting member 46, together with the counterweight 58, maintains the balance with the rotation moment of the support portion 16.

Similarly, as shown in FIG. 6, if the support portion 16 is moved upward as indicated by solid lines or downward as indicated by broken lines as shown in FIG. 6, the rotary connecting member 46 is moved up and down together with the weight connecting portion 50. Thus, the rotary connecting member 46, together with the counterweight 58, maintains the balance with the rotation moment of the support portion 16. When the rotary connecting member 46 moves left and right and up and down, a cylindrical member 47 rolls along a horizontal guide 50a of the weight connecting portion 50. Thus, the position of the support portion 16 can be changed without frictional resistance.

Since the position changing member is formed of one rotary connecting member 46, which moves in association with both the deformation of the link mechanism 24 and the rotation of the support column 20, the number of members of the entire medical instrument supporting apparatus 10 is less than that in the embodiment shown in FIGS. 1 to 3. Moreover, since the balance can be maintained against the position change of the medical instrument 8 in horizontal and vertical directions by the counterweight system comprising only one counterweight 58, the weight of the overall apparatus can be less. In this embodiment also, it is ensured that the medical instrument 8 can move easily and smoothly in the same manner as in the embodiment shown in FIGS. 1 to 4.

FIG. 7 shows a medical instrument supporting apparatus 10 according to still another embodiment.

The medical instrument supporting apparatus 10 of this embodiment is lighter than those of the above embodiments. The counterweight system of this embodiment is formed of an elastic member 72 which generates vertically downward force exerted on a weight connecting portion 50. In this embodiment, the elastic member 72 is formed of a compression coil spring, and keeps balance with a support portion 16 by force of repulsion against force in the compressing direction. One end of the elastic member 72 formed of the coil spring is fixed to a support column 20 and the other end thereof is fixed to an L-shaped shaft 62. The elastic member 72 exerts downward force on the weight connecting portion 50 via the L-shaped shaft 62. The horizontal component of the force is supported by a connecting slide 58a.

As shown in FIG. 7, the elastic member 72 is inclined with respect to a vertical axis O1. However, it may be arranged in parallel with the vertical axis O1, in which case the resistance on the connecting slide 58a can be smaller.

The medical instrument supporting apparatus 10, in which the counterweight system is formed of the resilient member 72, is very light. In the medical instrument supporting apparatus 10 of this embodiment, a base 18 is provided with a connecting member 19a and a fixing knob 19b to lock the connecting member 19a. The connecting member 19a is attached to a side rail R of a bed B on which a patient P lies, and can be fixed to the side rail R by the fixing knob 19b. The elastic member 72 is particularly advantageous in a case where the support column 20 is inclined with respect to the bed B. Even in this case, it is ensured that the elastic member 72 generates force along the vertical axis O1, so that the support portion 16 can move smoothly.

The counterweight system can be formed of only the elastic member 72. However, a counterweight used in the above-described embodiments may also be used together with the elastic member 72. In this case, the counterweight can be lighter. Further, the medical instrument supporting apparatus 10 as a whole can be lighter than in the embodiments described above, while the medical instrument 8 can be moved easily and smoothly.

Figure 8:
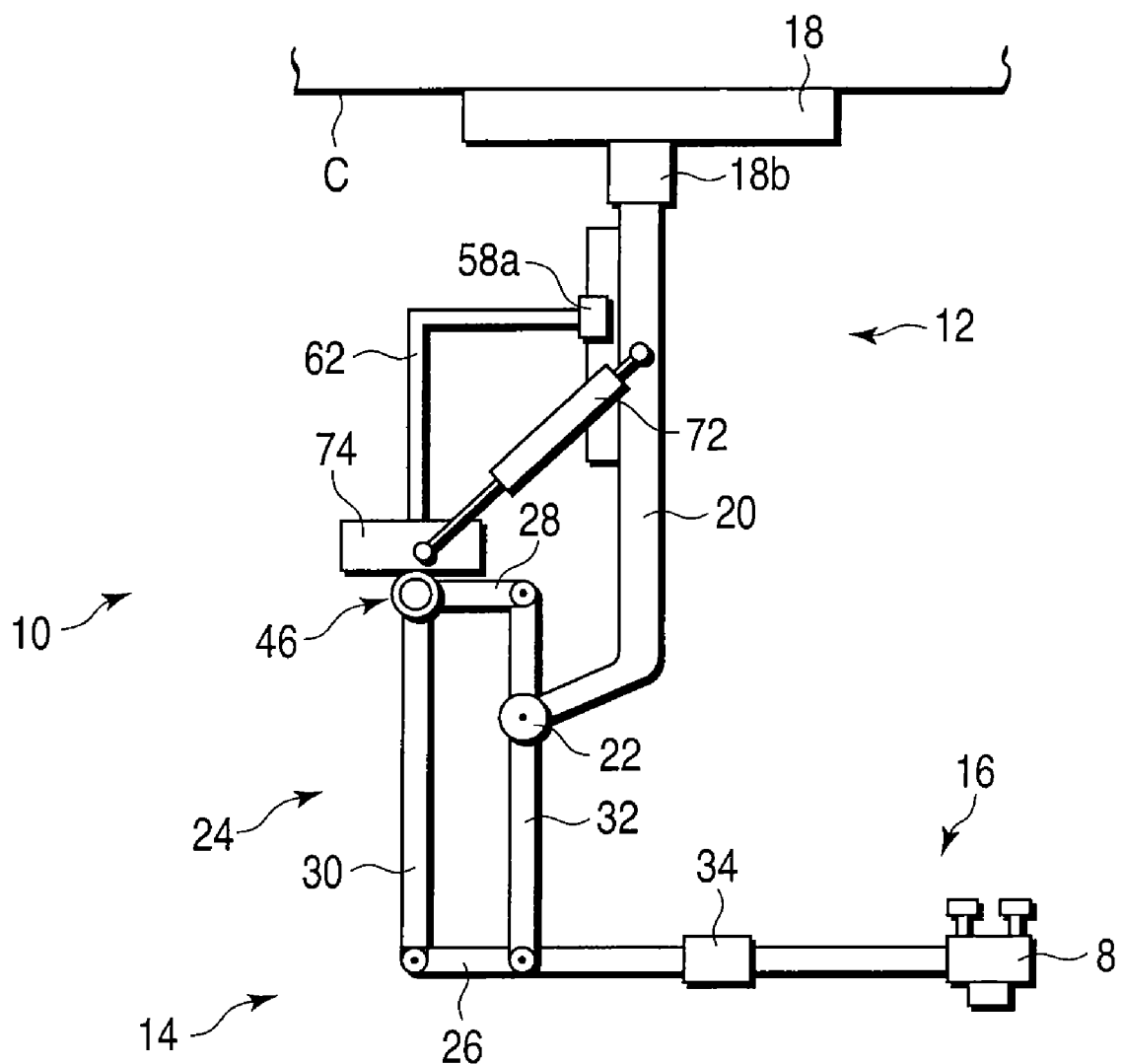
FIG. 8 is a schematic diagram showing a medical instrument supporting apparatus, which can be attached to a ceiling, according to still another embodiment.

FIG. 8 shows a medical instrument supporting apparatus 10 according to still another embodiment.

The medical instrument supporting apparatus 10 has a base 18, which is fixed to a ceiling C of a medical room. A support column 20 extends downward from the base 18 and an arm 14 is rotatably fixed to a distal end portion of the support column 20 via a support member 22. A surgical microscope as a medical instrument 8 is attached to a support portion 16 of the arm 14. A rotation moment in the clockwise direction about the support member 22 generated by the support portion 16 is balanced with a rotation moment in the counterclockwise direction generated by an elastic member 72 and exerted via a weight connecting portion 74 and a rotary connecting member 46.

With the configuration described above, the medical instrument 8 such as a microscope can freely be extended or contracted with excellent operability, regardless of the ambient environment, for example, even in a small space as well as in the above-described embodiments.

In this embodiment, the weight connecting portion 74 urges the rotary connecting member 46 downward from the side of the base 18 located above. Therefore, neither the frame portion 50b nor 52b in the above-described embodiments is required, and only a horizontal guide is required. Thus, the medical instrument supporting apparatus can be much lighter.

The members in the embodiments can be combined suitably, and should not be limited to any one of the embodiments.

For example, the elastic member 72 constituting the counterweight system is formed of the coil spring in the embodiment shown in FIG. 7 and the gas spring in the embodiment shown in FIG. 8. The elastic member 72 is not limited to those elements, but may be of any hydropneumatic type using gas pressure of air or the like or hydraulic pressure of oil or the like as a pressure generating medium. A plurality of elastic members 72 may be used in combination. Further, the elastic member 72 may be combined with a counterweight to constitute a counterweight system.

If a counterweight is used, a part or all of the counterweight may be formed integrally with the frame portions 50b or 52b of the weight connecting portion 50 or 52.

Further, the medical instrument supporting apparatus may be mounted on a medical trolley if necessary, so that it can be moved more easily to a required place.

Additional advantages and modifications will readily occur to those skilled in the art. Therefore, the invention in its broader aspects is not limited to the specific details and representative embodiments shown and described herein. Accordingly, various modifications may be made without departing from the spirit of the general inventive concept.

What is claimed is:

1. An apparatus for supporting a medical instrument, the apparatus comprising:
   a support column configured to be placed in one of a floor, a ceiling, a medical trolley and a bed;
   an arm supported by the support column and having a first end provided with a support portion configured to support a medical instrument and a second end, the arm being configured to move the support portion in horizontal directions and vertical directions relative to the support column;
   a position changing member provided at the second end of the arm and configured to move in accordance with movement of the support portion to a position corresponding to a position to which the support portion has been moved;
   a vertical guide portion provided at the support column; and
   a counterweight system including:
   a connecting slide connected to the vertical guide portion so as to be immovable in the horizontal directions and movable in the vertical directions relative to the support column,
   a weight connecting portion connected to the position changing member such that the position changing member is immovable in the vertical directions and movable in the horizontal directions relative to the weight connecting portion,
   an intermediate portion connecting the connecting slide and the weight connecting portion to each other, and
   a force generating portion configured to generate a vertically downward force to be exerted on the position changing member via at least the weight connecting portion of the connecting slide, the weight connecting portion and the intermediate portion,
   wherein the position changing member is configured to move in the horizontal directions relative to the counterweight system and to move in the vertical directions together with the counterweight system, and to keep a balanced state between the medical instrument supported by the support portion and the counterweight system when the first end of the arm is moved in the horizontal directions and the vertical directions.

2. The apparatus according to claim 1, wherein the force generating portion comprises a counterweight connected to at least one of the connecting slide, the weight connecting portion and the intermediate portion.

3. The apparatus according to claim 1, wherein the force generating portion includes a force generating member having a first end supported by the support column and a second end supported by at least one of the connecting slide, the weight connecting portion and the intermediate portion,
   the force generating member configured to generate the vertically downward force to be exerted on the position changing member via at least the weight connecting portion of the connecting slide, the weight connecting portion and the intermediate portion.

4. The apparatus according to claim 1, wherein the arm comprises a parallelogram link mechanism including a pivot rod rotatably attached to the support column, and the position changing member is connected to the parallelogram link mechanism and moves in association with deformation of the parallelogram link mechanism and rotation of the parallelogram link mechanism relative to the support column.

5. The apparatus according to claim 4, wherein the position changing member comprises a member which moves in association with both deformation of the parallelogram link mechanism and rotation of the parallelogram link mechanism relative to the support column.

6. The apparatus according to claim 4, wherein the position changing member comprises a deformation associating member which moves in association with deformation of the parallelogram link mechanism and a rotation associating member which moves in association with rotation of the parallelogram link mechanism relative to the support column.

7. The apparatus according to claim 1, wherein the position changing member comprises a cylindrical member configured to rotate about a central axis of the cylindrical member, and
   the weight connecting portion comprises a horizontal guide,
   wherein the cylindrical member is configured to roll about the central axis of the cylindrical member so as to slide along the horizontal guide.

8. The apparatus according to claim 1, wherein the arm comprises a tilting mechanism configured to tilt the support portion about three axes perpendicular to one other.

9. The apparatus according to claim 1, wherein the medical instrument includes at least one of a microscope, an endoscope, a medical display and a medical treatment tool.

10. The apparatus according to claim 1, wherein the support column is configured to be rotatable about a vertical axis extending in a vertical direction and be kept at a rotational position.

* * * * *